US010137439B2

(12) United States Patent
Ramprasad

(10) Patent No.: US 10,137,439 B2
(45) Date of Patent: Nov. 27, 2018

(54) PROCESS AND CATALYST FOR THE PRODUCTION OF PYRIDINE AND ALKYL DERIVATIVES THEREOF

(71) Applicant: W. R. GRACE & CO.-CONN., Columbia, MD (US)

(72) Inventor: Dorai Ramprasad, Columbia, MD (US)

(73) Assignee: W. R. GRACE & CO.-CONN., Columbia, MD (US)

( * ) Notice: Subject to any disclaimer, the term of this patent is extended or adjusted under 35 U.S.C. 154(b) by 0 days.

(21) Appl. No.: 15/435,714

(22) Filed: Feb. 17, 2017

(65) Prior Publication Data

US 2017/0157599 A1 Jun. 8, 2017

Related U.S. Application Data

(62) Division of application No. 14/437,997, filed as application No. PCT/US2013/066593 on Oct. 24, 2013, now Pat. No. 9,598,366.

(60) Provisional application No. 61/718,385, filed on Oct. 25, 2012.

(51) Int. Cl.
*B01J 29/40* (2006.01)
*C07D 213/09* (2006.01)
*C07D 213/10* (2006.01)
*B01J 37/08* (2006.01)
*B01J 37/00* (2006.01)

(52) U.S. Cl.
CPC ......... *B01J 29/405* (2013.01); *B01J 37/0045* (2013.01); *B01J 37/08* (2013.01); *C07D 213/10* (2013.01); *B01J 2229/18* (2013.01); *B01J 2229/20* (2013.01); *B01J 2229/42* (2013.01)

(58) Field of Classification Search
CPC ...... B01J 37/08; B01J 2229/18; B01J 29/405; B01J 2229/20; C07D 213/09; C07D 213/10
USPC ..................... 546/251; 502/60, 77
See application file for complete search history.

(56) References Cited

U.S. PATENT DOCUMENTS

| | | | |
|---|---|---|---|
| 3,272,825 A | 9/1966 | Shimizu et al. | 260/290 |
| 3,946,020 A | 5/1976 | Minato et al. | 260/290 |
| 4,089,863 A | 5/1978 | Darragh | 260/290 |
| 4,220,783 A | 9/1980 | Chang et al. | 546/251 |
| 4,675,410 A | 6/1987 | Feitler et al. | 546/251 |
| 4,765,884 A | 8/1988 | Walker et al. | 208/89 |
| 4,810,794 A | 3/1989 | Shimizu et al. | 546/251 |
| 4,861,894 A | 8/1989 | Bowes et al. | 546/251 |
| 4,873,211 A | 10/1989 | Walker et al. | 502/64 |
| 4,985,384 A | 1/1991 | Gilson | |
| 5,013,843 A | 5/1991 | Feitler et al. | 546/251 |
| 5,110,776 A | 5/1992 | Chitnis et al. | 502/64 |
| 5,126,298 A | 6/1992 | Absil et al. | 502/68 |
| 5,218,122 A | 6/1993 | Goe et al. | 546/251 |
| 5,237,068 A | 8/1993 | Shimizu et al. | |
| 5,780,635 A | 7/1998 | McAteer et al. | 546/251 |
| 5,969,143 A | 10/1999 | Chester et al. | 546/260 |
| 6,156,689 A | 12/2000 | Kimble | |
| 7,297,828 B2 | 11/2007 | Euzen et al. | 585/467 |
| 7,459,412 B2 | 12/2008 | Lercher et al. | 502/60 |
| 8,030,238 B2 | 10/2011 | Spano et al. | 502/60 |
| 8,901,026 B2 | 12/2014 | Wormsbecher et al. | |
| 2002/0049133 A1 | 4/2002 | Ziebarth et al. | 502/64 |
| 2002/0173660 A1 | 11/2002 | Kulkarni et al. | |
| 2004/0121902 A1 | 6/2004 | Chang et al. | 502/206 |
| 2007/0276173 A1 | 11/2007 | Spano et al. | 585/438 |
| 2010/0264066 A1 | 10/2010 | Kumar | |
| 2011/0108462 A1 | 5/2011 | Chang | 208/113 |

FOREIGN PATENT DOCUMENTS

CN 101347744 1/2009
WO WO2011072469 6/2011

OTHER PUBLICATIONS

Parry; An Infrared Study of Pyridine Absorbed on Acidic Solids. Characterization of Surface Acidity, Journal of Catalyst, vol. 2, pp. 371-379 (1963).
Riseman; Fourier Transform Infrared Photoacoustic Spectroscopy of Pyridine Absorbed on Silica-Alumina and γ-Alumbia, J. Phys. Chem. 86, 1760-1763 (1982).
Li; Applied Catalysis, A: General, 2009, 360, 8-16.
Amin; Journal of Natural Gas Chemistry, 2003, 12, 123-134.
Biscardi; Journal of Catalysis, 1998, 179, 192-202.
El-Malki; J. Phys. Chem. B, 1999, 103, 4611-4622.
Shimazu; Microporous and Mesoporous Materials 1998, 21, 447-451.
Jin; Applied Catalysis, A: General 2008, 350, 71-78.
Jin; Catalysis Letters 2009, 131, 545-551.
Jin; Gaoxiao Huaxue Gongcheng Xuebao, 2010, 24, 226-232, CAS Abstract, Accession No. 2010:618408.
Liu; "Effect of ZSM-5 on the aromatization performance in cracking catalyst", Journal of Molecular Catalysis A: Chemical, 2004.

(Continued)

*Primary Examiner* — Daniel R Carcanague
(74) *Attorney, Agent, or Firm* — Charles A. Cross

(57) ABSTRACT

A process for increasing the overall yield of pyridine or its alkyl pyridine derivatives during a base synthesis reaction is disclosed. The process comprises reacting a $C_2$ to $C_5$ aldehyde, a $C_3$ to $C_5$ ketone or a combination thereof, with ammonia and, optionally, formaldehyde, in the gas phase and in the presence of an effective amount of a particulate catalyst comprising a zeolite, zinc, a binder, and clay and optionally a matrix, wherein the catalyst has a L/B ratio of about 1.5 to about 4.0. Preferably, the zeolite is ZSM-5. A process for enhancing the catalytic activity of a zinc and zeolite containing catalyst to increase the overall yield of pyridine and/or its derivatives during a base synthesis reaction is also disclosed.

19 Claims, No Drawings

(56) References Cited

OTHER PUBLICATIONS

Slobodnik; "Synthesis of Pyridines over Zeolites in Gas Phase". Collect. Czech Chem Commun 2007, vol. 72, Nos. 5-6, 618-628.
Slobodnik; "Synthesis of pyridines over modified ZSM-5 catalysts", Studies in Surface Science and Catalysis 2005, vol. 158, 1835-1842.
Shen; "Study on the synthesis of pyridine derivative and catalyst thereof", China Master's Thesis Full-text Database, Engineer Science I, No. 3, p. 4, 13-16, 27, 53-55 and 63, 2003.
Sheldon and H. van Bekkum, Fine Chemicals through Heterogeneous Catalysis, Ed:, Wiley (2001) pp. 277-183.

PROCESS AND CATALYST FOR THE PRODUCTION OF PYRIDINE AND ALKYL DERIVATIVES THEREOF

CROSS REFERENCE TO RELATED APPLICATIONS

This application is a divisional of U.S. application Ser. No. 14/437,997, filed Apr. 23, 2015, which claims the benefit of the filing date of International Application No. PCT/US2013/066593 filed Oct. 24, 2013, and U.S. Provisional Patent Application No. 61/718,385 filed Oct. 25, 2012, entitled "PROCESS AND CATALYST FOR THE PRODUCTION OF PYRIDINE AND ALKYL DERIVATIVES THEREOF", the disclosure of which is hereby incorporated by reference.

FIELD OF THE INVENTION

The present invention relates to an improved process for pyridine base synthesis, and to specified zinc containing zeolite based catalysts for use in the same.

BACKGROUND OF THE INVENTION

Nitrogen-containing compounds are used as structural components of pharmaceuticals and agrochemicals due to their high biological activity. Among these compounds, pyridine bases are produced in by far the largest quantity and are used in various applications such herbicides, insecticides, pharmaceuticals and adhesives.

The base synthesis of pyridine and its derivatives is well known. The process generally involves reacting aldehydes and/or ketones with ammonia in the gas phase using a heterogeneous catalyst either in a fixed bed or fluidized bed reactor at temperatures ranging from about 400° C. to about 450° C. The reaction generates coke and the catalyst has to be regenerated with air. The use of a fluidized bed provides a useful continuous regeneration system.

Catalysts used in pyridine base synthesis reactions have varied from alumina either alone or as a support, to amorphous silica alumina (see e.g., U.S. Pat. Nos. 3,272,825; 3,946,020; and 4,089,863) and/or metal substituted silica alumina (see e.g., R. A. Sheldon and H. van Bekkum, *Fine Chemicals through Heterogeneous Catalysis*, Ed, Wiley p 277). However, in recent years, the focus has shifted to the use of so-called "shape selective" zeolite, e.g. aluminosilicates of a definite crystal structure and pore size and characteristic, based catalyst systems. A major breakthrough in this area came with the use of the zeolite ZSM-5, also called "MFI", which showed improved pyridine yields in the pyridine beta reaction due to the shape selectivity offered by the size and two dimensional pore channels of the zeolite (see e.g., U.S. Pat. Nos. 4,220,783; and 4,675,410). Improved pyridine yields were found in ZSM-5 zeolites having silica/alumina ratios between 150-400 (see e.g., R. A. Sheldon, H. van Bekkum, *Fine Chemicals through Heterogeneous Catalysis*, Ed: Wiley p 277). Further improvements were seen in the development of metal substituted ZSM-5 zeolites. For example, zeolites ion-exchanged with thallium, lead or cobalt showed increased yields of pyridine bases (see e.g., U.S. Pat. No. 4,810,794). Other metal substituted zeolites used in pyridine catalysts have included ZSM-5 zeolites modified with one or more metal ions of zinc, tin or tungsten. (see for example, U.S. Pat. No. 5,218,122).

Because it uses inexpensive and widely available raw materials, base synthesis of pyridine continues to provide good prospect to meet the growing demands for pyridine and its alkyl derivatives. However, there remains a need for improved processes and catalysts which are useful to enhance product yields of pyridine and alkyl pyridine derivatives during base synthesis reactions.

SUMMARY OF THE INVENTION

The essence of the present invention lies in the discovery that a relationship exists between the Lewis (L) acid to Bronsted (B) acid ratio (L/B ratio) and the catalytic activity of a zinc modified zeolite based catalyst to increase the overall yields of pyridine during a base synthesis reaction. Unexpectedly, it has been discovered that a zinc modified zeolite based catalyst having an L/B ratio ranging from about 1.5 to about 4.0 exhibits a significant improvement in pyridine yield as compared to yields obtainable using a zeolite based catalyst containing no zinc. Zinc modified zeolite based catalysts in accordance with the invention also exhibit an activity for overall yield increases of pyridine when compared to the activity of similarly zinc modified zeolite based catalysts having a L/B ratio of less than about 1.5 or greater than about 4.0.

Accordingly, it is an advantage of the present invention is to provide a process of increasing the overall yields of pyridine or its alkyl pyridine derivatives during a base synthesis reaction. In accordance with the process of the invention, alkyl aldehydes and/or ketones are reacted with ammonia, and optionally, formaldehyde, in a gas phase in the presence of an effective amount of a zinc modified zeolite based catalyst having an L/B ratio ranging from about 1.5 to about 4.0.

Another advantage of the present invention to provide catalyst compositions having improved catalytic ability to increase the overall yields of pyridine and its derivatives during a base synthesis process. Catalysts of the invention generally comprise a ZSM-5 and/or ZSM-11 zeolite, zinc, a binder, clay and optionally a matrix material. In a preferred embodiment of the invention, the zeolite is ZSM-5. Catalyst compositions of the invention possess an L/B ratio ranging from about 1.5 to about 4.0. Advantageously, higher overall yields of pyridine and its alkyl pyridine derivatives are achievable during a base synthesis reaction using the invention catalyst than yields obtainable using a zeolite based catalyst containing no zinc or zinc modified zeolite based catalysts having an L/B ratio of less than about 1.5 or greater than about 4.0.

Yet another advantage of the present invention is to provide a method of enhancing the catalytic activity of a zinc containing zeolite based catalyst to produce increased overall yields of pyridine and its alkyl pyridine derivatives during a base synthesis reaction. The method involves adjusting the components of the catalyst to provide specified L/B ratios, as measured by diffuse reflectance IR spectrum, in the catalyst composition, which ratios unexpectedly correlate to an increase in the overall yields of pyridine bases during a base synthesis reaction.

These and other related advantages and variations of the detailed aspects of the present invention will become apparent from the following description as described in further details below.

DETAILED DESCRIPTION OF THE INVENTION

The present invention is directed to improved processes and catalyst compositions for use therein which provides an increase in the overall yields of pyridine and its alkyl derivatives during a base synthesis reaction. In accordance with the process, base synthesis of pyridine and its alkyl derivatives is conducted in the presence of an effective amount of a particulate zinc containing zeolite based catalyst having a specified L/B ratio. Catalyst compositions useful in the present invention generally comprises a ZSM-5 and/or a ZSM-11 zeolite, zinc, a binder, clay and optionally, a matrix material, in amounts sufficient to provide the specified L/B ratio.

For purposes of this invention, the term "base synthesis" is used herein to identify a process by which bases of pyridine or alkyl pyridine are prepared by reacting aldehydes and/or ketones with ammonia in the gas phase using a heterogeneous catalyst. Some examples of base synthesis reactions (and their common names where appropriate) include: the synthesis of pyridine and beta-picoline from acetaldehyde and formaldehyde (the "pyridine-beta reaction"); the synthesis of alpha- and gamma-picoline from acetaldehyde (the "alpha-gamma reaction"); the synthesis of 2,6-dimethylpyridine ("2,6-lutidine") from acetone and formaldehyde; the synthesis of 2,4,6-trimethylpyridine ("sym-collidine") from acetone alone or with acetaldehyde; the synthesis of pyridine and beta-picoline from acrolein alone or with acetaldehyde; the synthesis of 3,5-dimethylpyridine from propionaldehyde and formaldehyde; and the synthesis of beta-picoline from acetaldehyde, formaldehyde and propionaldehyde. Many others are known and reported or practiced in the art, and are equally considered within the scope of the description and invention herein.

Zeolites useful to prepare catalysts in accordance with the invention generally include ZSM-5 and/or ZSM-11 zeolites. In a preferred embodiment of the invention, the zeolite is ZSM-5.

In one embodiment of the invention, the zeolites useful to prepare catalyst of the invention possess a silica to alumina ratio of about 100 or less. In a preferred embodiment, the zeolites have a silica to alumina ratio of about 20 to about 80. In an even more preferred embodiment of the invention, the zeolites possess a silica to alumina ratio of about 28 to about 55.

Primarily, the binder performs the all important function of holding the components of the catalyst compositions together. However, it is within the scope of the invention that the binder may also provide some catalytic activity. Suitable binders contemplated for use in the catalyst compositions of the invention typically include, but are not limited, to silica, alumina, silica-alumina and combinations thereof. In a preferred embodiment, the binder is alumina. Preferably, the alumina binder is a gamma alumina that has been derived from an aluminum sol, colloidal alumina, peptized alumina, aluminum chlorohydrate and/or other aluminum precursors.

Catalysts useful in the present invention also include clay. While kaolin is the preferred clay component, it is also contemplated that other clays, such as pillard clays and/or modified kaolin (e.g. metakaolin), may be included in catalyst compositions useful in the present invention.

It is also within the scope of the invention, that in additional to clay, a matrix material may optionally be present in catalyst compositions useful in the present invention. When present, suitable matrix materials include metal oxides, e.g. alumina, silica, silica-alumina, oxides of transition metals and combinations thereof. Preferably, the matrix materials include alumina, silica, silica-alumina and combinations thereof.

Catalyst compositions useful in the present invention have an L/B ratio of about 1.5 to about 4.0. In a preferred embodiment of the invention, the catalyst compositions have an L/B ratio ranging from about 2.0 to about 3.6. The L/B ratio may be obtained by adjusting the concentration of any or all of the catalyst components during catalyst formulation to provide the desired L/B ratio. The L/B/ ratio may be measured using diffuse reflectance IR spectrum to determine the ratio of the height of the 1450 cm−1 peak L=(Lewis acid sites) to the 1550 cm−1 peak B=(Bronsted acid sites).

The particulate catalyst compositions of the invention are useful in a base synthesis process typically operated in a fixed bed or fluidized bed reactor, e.g. FCC catalytic cracking unit, to achieve an overall increase in pyridine and alkyl pyridine yields. The catalyst compositions are typically in the form of spherical particles and have a particle size and an attrition property sufficient to affect fluidization properties within a fixed bed or fluidized bed reactor. When used in a fluidized bed reactor, catalyst compositions of the invention will typically have a mean particle size of about 40 μm to about 200 μm. In a preferred embodiment of the invention, the catalyst compositions have a mean particles size ranging from about 60 μm to about 120 μm.

Catalyst compositions used in the present invention will possess an attrition resistance, as measured by Davison Index (DI), sufficient to maintain the structural integrity of the compositions in the fixed bed or fluidized bed reactor. Typically, a DI value of less than 20 will be sufficient. In a preferred embodiment of the invention, the DI value is less than 10.

The amounts of each of the components in the catalyst compositions will vary depending on such factors as the desired L/B ratio, the particle size, the attrition resistance, the reactor to be used, etc. Generally, the amounts of zeolite, zinc, binder, clay and optionally matrix components present in the catalyst compositions used in the invention will vary within a wide range, e.g. about 1-99% by weight, respectively for each component, based upon the total weight of the composition, provided however, that each component is used in an amount sufficient to provide the desired L/B ratio, particle size and attrition resistance for use of the final catalyst composition in a fixed bed or, preferably, a fluidized bed reactor. In a preferred embodiment of the invention, the amount of zeolite ranges from about 35 wt % to about 50 wt % of the catalyst composition. The binder amount ranges from about 10 wt % to about 30 wt % of the catalyst composition. The clay component will preferably comprise from about 30 wt % to about 50 wt % of the total catalyst composition. When used, the matrix material will typically comprise the remainder of the catalyst. All of said weight percentages recited herein above is based on the total weight of the final catalyst composition.

Zinc may be incorporated into the catalyst composition by treatment on the zeolite before or after the zeolite is formulated with the binder, clay and optionally matrix components to prepare the final catalyst compositions. Alternatively, zinc may be incorporated during catalyst formulation as a component of the catalyst. Further, zinc may be exchanged onto the preformed catalyst following catalyst formulation.

Where the zeolite is treated with zinc prior to catalyst formulation, the zeolite may be modified through treatment with metal ions or compounds of zinc. Suitable zinc compounds include, but are not limited to, soluble salts such as nitrates, halides or acetates. Treatment of the zeolites may be carried out in any number of ways known in the art (such as for example, U.S. Pat. No. 5,218,122, said patent herein incorporated by reference in its entirety) and may be carried out several times if desired to ensure substantial metal uptake on the zeolite.

In one embodiment, the zeolite is added to an aqueous solution of the desired amount of zinc compound in stoichiometric excess to obtain a mixture. Optionally, the mixture is heated at a predetermined temperature and time with stirring. The mixture is filtered, rinsed, dried and then calcined at elevated temperature, e.g. about 100° C. to about 600° C. to obtain the modified zeolite.

In another embodiment of the invention, a physical mixture of the zeolite and the desired zinc salt is accomplished either dry or in the presence of water in an amount sufficient to obtain a paste or similar consistency, by blending, mixing or other suitable physical means. These and other similar procedures are well known within the catalysis arts and are all within the scope of the invention.

The final catalyst compositions may be prepared by any conventional means known in the catalysis arts. In a preferred embodiment of the invention, catalyst compositions in accordance with the present invention are formed from an aqueous slurry which comprises an amount by weight of the zeolite, optionally zinc, binder, clay and optional matrix materials. The amounts of the catalyst components, i.e. zeolite, optionally zinc, binder, clay and optional matrix materials, are adjusted in the slurry to provide an amount of each component sufficient to obtain the desired L/B ratio, particle size and attrition resistance in the final catalyst composition.

Zinc may be present in the slurry as zinc ions pre-exchanged on the zeolite prior to incorporation into the aqueous slurry as described herein above. In the alternative, zinc may be present in the aqueous slurry as a component thereof in the form of a salt solution of zinc, e.g. zinc nitrates, halides and/or acetates as described herein above.

The aqueous slurry is subjected to a spraying step using conventional spray drying techniques. During the spray drying step, the slurry is converted to a particulate solid composition. The spray dried catalyst particles typically have an average particle size on the order of about 40 to about 200 μm. Following spray drying, the catalyst particles are calcined at temperatures ranging from about 150° C. to about 600° C. for a period of about 4 hours to about 10 minutes.

Where the zinc has not been previously incorporated into catalyst, the preformed catalyst particles may be ion exchanged with zinc, in the amount desired in the final catalyst composition. Alternatively, the catalyst particles may be impregnated, e.g. via incipient wetness, with an aqueous salt solution of zinc to impregnate zinc ions onto the calcined catalyst particles. The catalyst particles may thereafter by washed, preferably with water and the washed catalyst particles are separated from the slurry by conventional techniques, e.g. filtration, and dried to lower the moisture content of the particles.

The process of the invention provides an increase in the overall yields of pyridine or its alkyl pyridine derivatives produced during a base synthesis reaction. Significant improvement in overall pyridine yields, i.e. greater than 2%, were achieved when compared to yields obtained using a zeolite based heterogeneous catalyst which contain no zinc. Improved overall pyridine yields, i.e. greater than 70%, were also achieved over similar zinc containing zeolite based catalyst having a L/B ratio of less than about 1.5 or greater than about 4.0.

In accordance with the process of the invention, alkyl aldehydes and/or ketones are reacted with ammonia, and optionally, formaldehyde, in a gas phase in the presence of an effective amount of a particulate catalyst composition as described hereinabove in fixed bed or fluidized bed reactor to achieve an unexpected overall increase in yields of pyridine and it alkyl derivatives. The equipment set up and operation of fluid-bed reactors vary according to many factors tied to the particular reaction under consideration. The same are readily constructed by those of ordinary skill in the art, and are all within the scope of the invention herein. Reaction parameters such as temperature, feed mole ratios, feed velocity and contact time and the like vary over a wide range of operable conditions also well known and within the scope of the invention.

As previously discussed, many base synthesis processes are known and are also contemplated to be within the scope of the invention herein. In addition to the specific Examples below and to the disclosures incorporated by reference above, for the pyridine-beta synthesis it is generally preferred that a feed of formaldehyde to acetaldehyde in a mole ratio of at least about 1:1 is used. The addition of methanol to the extent of about 5 to 70% of the formaldehyde component is also preferred, as originally described in U.S. Pat. No. 2,807,618. At least a portion of the formaldehyde can further be replaced by paraformaldehyde or symtrioxane, and water can be present as desired to provide a stable, storable solution. Ammonia is supplied in a ratio of at least about 0.6:1 to the total organic components in the feed, with a range of about 0.7 to 1.5 being more preferred and about 0.8 to 1.2 being most preferred from testing to date. The feed rate is in turn chosen to give good fluidization of the bed, usually in the range of a superficial velocity between about 0.3 to 4.0 ft./sec. Temperature of the reaction is preferably between about 350° C. and 550° C. more preferably between about 400° C. and 500° C. and most preferably at about 450° C. The products of the reaction, being pyridine and beta-picoline, are condensed and separated into pure compounds by drying and distillation as is well known in the art. By way of a second example, the alpha-gamma reaction is preferably carried out in much the same way except that formaldehyde and methanol are left out of the feed mixture.

To further illustrate the present invention and the advantages thereof, the following specific examples are given. The examples are given as specific illustrations of the claimed invention. It should be understood, however, that the invention is not limited to the specific details set forth in the examples.

All parts and percentages in the examples as well as the remainder of the specification that refers to solid compositions or concentrations are by weight unless otherwise specified. However, all parts and percentages in the examples as well as the remainder of the specification referring to gas compositions are molar or by volume unless otherwise specified.

Further, any range of numbers recited in the specification or claims, such as that representing a particular set of properties, units of measure, conditions, physical states or percentages, is intended to literally incorporate expressly herein by reference or otherwise, any number falling within such range, including any subset of numbers within any range so recited.

EXAMPLES

Example 1

Catalysts A, B, C, D and E were prepared using ZSM-5 with a silica/alumina ratio of 28 or 55. Zinc chloride was added into an aqueous slurry of zeolite, an alumina binder and clay and the slurry was spray dried using standard spray drying procedures. The spray dried particles were calcined at a temperature of 593.3° C. (1100° F.) to obtain the final catalysts. Compositions of the catalysts following spray drying and calcination were as shown in Table 1 below.

TABLE 1

| CATALYST | ZSM-5  | Alumina | Clay | ZnO  |
|----------|--------|---------|------|------|
| A        | 39.4*  | 11.8    | 47.3 | 1.42 |
| B        | 39.0*  | 11.7    | 46.8 | 2.32 |
| C        | 39.4** | 11.8    | 48.3 | 0.53 |
| D        | 39.4** | 11.8    | 47.8 | 1.12 |
| E        | 39.4** | 11.8    | 47.3 | 1.69 |

*silica/alumina = 28
**silica/alumina = 55

Example 2

The catalyst samples obtained in Example 1 above and a control catalyst sample (no zinc) were analyzed using diffuse reflectance IR spectropscopy. The procedure was as follows: Approximately one gram of sample was placed in a ceramic crucible which was placed in a specially designed quartz cell. The samples were calcined for one hour at 500° C. then for one hour under vacuum. The samples were returned to room temperature and were exposed to a pyridine saturated stream of helium for 30 minutes. The physisorbed pyridine was then removed by heating the samples to 200° C. for two hours under vacuum. Peak height was measured by placing the curser at the peak maximum and adjusting the baseline. The L/B (Lewis/Bronsted) ratio was measured by comparing the height of the 1450 cm−1 peak L=(Lewis acid sites) to the 1550 cm−1 peak B=(Bronsted acid sites). Results were as recorded in Table 2 below.

TABLE 2

| CATALYST | L/B RATIO |
|----------|-----------|
| No Zinc  | 0.57      |
| A        | 3.3       |
| B        | 6.0       |
| C        | 1.1       |
| D        | 2.1       |
| E        | 3.1       |

Example 3

The performance of the catalysts was evaluated and correlated to L/B ratios. The procedure for testing the catalysts in a fluidized bed reactor was as described in U.S. Pat. No. 4,675,410, the disclosure of which is herein incorporated by reference in its entirety. The catalyst formulations as described in Example 1 above and the control catalyst were loaded into the fluid bed reactor. The catalysts were heated under a nitrogen flow of ~60 liter per hours to a temperature of ~450° C. A mixture of acetaladeldhyde and formaldehyde was passed through a vaporized into the reactor. The nitrogen flow into the reactor was replaced with an ammonia flow at a rate of ~111 g/hr. Pyridine yields were calculated as Yield %=total C atoms in Product×100/total C atoms in feed. Results are recorded in Table 3 below.

TABLE 3

| CATALYST        | L/B  | Yield improvement |
|-----------------|------|-------------------|
| Control - no zinc | 0.57 | —                 |
| A               | 3.3  | 2-4%              |
| B               | 6.0  | 0-1%              |
| C               | 1.1  | 1-2%              |
| D               | 2.1  | 2-4%              |
| E               | 3.1  | 2-4%              |

The data shows that catalysts having an L/B ratio between about 1.5 to about 4.0 achieved overall yield improvements of 2% or greater as compared to the control which contained no zinc. While catalyst containing zinc but having an L/B ratio outside of the range of the invention, i.e., of about less than 1.5 and greater than about 4.0, showed increase yields as compared to the control, they showed inferior overall yields of pyridine bases when compared to yields obtained using the process and catalyst of the present invention.

The invention claimed is:

1. A method of enhancing the catalytic activity of zinc containing zeolite-based heterogeneous catalyst for the production of pyridine and its alkyl derivatives during a base synthesis reaction, the method comprising:
    (1) preparing an aqueous slurry comprising components (a) a zeolite selected the group consisting of ZSM-5, ZSM-11 and combinations thereof, (b) optionally zinc, (c) a binder and (d) clay in amounts sufficient to provide an L/B ratio of about 1.5 to about 4.0 in the final catalyst composition;
    (2) spray drying the slurry to provide catalyst particles having a particle size of about 40 μm to about 200 μm;
    (3) calcining the particles to provide a final catalyst composition having an L/B ratio of about 1.5 to about 4.0.

2. The method of claim 1 wherein the zeolite component in the aqueous slurry of step (1) is ZSM-5.

3. The method of claim 1 wherein the zeolite has been treated with a compound of zinc prior to incorporation into the aqueous slurry of step (1).

4. The method of claim 1 wherein a compound of zinc is incorporated as a component of the aqueous slurry of step (1).

5. The method of claim 1 comprising further ion exchanging a compound of zinc on the calcined catalyst particles.

6. The method of claim 3 wherein the compound of zinc is selected from the group consisting of nitrate, halides, acetates and combinations thereof.

7. The method of claim 4 wherein the compound of zinc is selected from the group consisting of nitrate, halides, acetates and combinations thereof.

8. The method of claim 5 wherein the compound of zinc is selected from the group consisting of nitrate, halides, acetates and combinations thereof.

9. The method of claim 1 wherein the final catalyst particles have an L/B ratio of about 2.0 to about 3.6.

10. The method of claim 1 wherein the binder is a material selected from the group consisting of aluminum sol, colloidal alumina, aluminum chlorohydrate and combinations thereof.

11. The method of claim 1 wherein the zeolite has a silica to alumina ratio of about 100 or less.

12. The method of claim 11 wherein the zeolite has a silica/alumina ratio of from about 20 to about 80.

13. The method of claim 2 wherein the zeolite has a silica/alumina ratio of about 28 to about 55.

14. The method of claim 1 wherein the shiny of step (1) further comprises a matrix material.

15. The method of claim 1 wherein the clay is kaolin clay.

16. The method of claim 1 wherein the zeolite is present in the aqueous slurry of step (1) an amount sufficient to provide from about 35 wt % to about 50 wt % zeolite based on the total weight of the final catalyst composition.

17. The method of claim 1 wherein the binder is present in the aqueous slurry of step (1) in an amount sufficient to provide from about 10 wt % to about 30 wt % binder based on the total weight of the final catalyst composition.

18. The method of claim 1 wherein the clay component is present in the aqueous slurry of step (I) in an amount sufficient to provide from about 30 wt % to about wt % clay based on the total weight of the final catalyst composition.

19. The method of claim 1 wherein the final catalyst composition has a DI of less than 20.

* * * * *